(12) United States Patent
Morrison et al.

(10) Patent No.: US 8,785,131 B2
(45) Date of Patent: Jul. 22, 2014

(54) PROGNOSTIC TEST FOR EARLY STAGE NON SMALL CELL LUNG CANCER (NSCLC)

(75) Inventors: Larry E. Morrison, Lombard, IL (US); John Coon, Oak Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 548 days.

(21) Appl. No.: 12/268,797

(22) Filed: Nov. 11, 2008

(65) Prior Publication Data
US 2010/0120027 A1 May 13, 2010

(51) Int. Cl.
*C12Q 1/68* (2006.01)
*C07H 21/02* (2006.01)

(52) U.S. Cl.
USPC ........................................ 435/6.12; 536/23.1

(58) Field of Classification Search
USPC .................................... 435/6, 6.12; 536/23.1
See application file for complete search history.

(56) References Cited

U.S. PATENT DOCUMENTS

| | | | |
|---|---|---|---|
| 5,491,224 A | 2/1996 | Bittner et al. | |
| 5,506,350 A | 4/1996 | Bittner et al. | |
| 5,756,696 A | 5/1998 | Gray et al. | |
| 5,776,688 A | 7/1998 | Bittner et al. | |
| 6,174,681 B1 | 1/2001 | Halling et al. | |
| 6,797,471 B2 * | 9/2004 | Katz et al. | 435/6 |
| 2003/0087248 A1 * | 5/2003 | Morrison et al. | 435/6 |
| 2005/0147995 A1 * | 7/2005 | Steck et al. | 435/6 |
| 2006/0063194 A1 | 3/2006 | Abbott | |
| 2007/0275403 A1 | 11/2007 | Abbott | |
| 2008/0182257 A1 * | 7/2008 | Bastian et al. | 435/6 |
| 2009/0258350 A1 | 10/2009 | Abbott | |
| 2010/0317002 A1 * | 12/2010 | Daniely et al. | 435/6 |

FOREIGN PATENT DOCUMENTS

| | | |
|---|---|---|
| WO | 2005117553 A2 | 12/2005 |
| WO | 2006128195 A2 | 11/2006 |
| WO | 2011006058 A1 | 1/2011 |

OTHER PUBLICATIONS

Carison et al. Americon J. of Pathology, 2000, vol. 157(3), p. 973-983.*
Romeo et al. J. of Molecular Diagnostics, 2003, vol. 5(2), p. 103-112.*
Yoshimoto et al. Cancer Genetics and Cytogenetics, 2006, vol. 169, p. 128-137.*
SORIA, Clin Cancer Res, 2002, v8, pp. 1178-1184.
Endoh et al., J. of Thoracic Oncology, 2006, vol. 1, No. 7, 629-634.
Ding L., et al., "Somatic Mutations Affect Key Pathways in Lung Adenocarcinoma," Nature, 2008, vol. 455 (7216), pp. 1069-1075.
McDermott U., et al., "Identification of Genotype-Correlated Sensitivity to Selective Kinase Inhibitors by Using High-throughput Tumor Cell Line Profiling," Proceedings of the National Academy of Sciences, 2007, vol. 104 (50), pp. 19936-19941.
She Q.B., et al., "Resistance to Gefitinib in PTEN-null HER-Overexpressing Tumor Cells can be Overcome through Restoration of PTEN Function or Pharmacologic Modulation of Constitutive Phosphatidylinositol 3'-Kinase/Akt Pathway Signaling," 2003, vol. 9 (12), pp. 4340-4346.
Sos M.L., et al., "PTEN Loss Contributes to Erlotinib Resistance in EGFR-Mutant Lung Cancer by Activation of Akt and EGFR," Cancer Research, vol. 69 (8), pp. 3256-3261, 2009.
Thisted R.A., "What is a P-Value?" www.stat.uchicago.edu/~thisted 1998, pp. 1-6.
Yamamoto H., et al., "PIK3CA Mutations and Copy Number Gains in Human Lung Cancers," Cancer Research, 2008, vol. 68 (17), pp. 6913-6921.
Zudaire I., et al., "Molecular Characterization Of Small Peripheral Lung Tumors Based On The Analysis Of Fine Needle Aspirates," Histology And Histopathology, 2008, vol. 23 (1), pp. 33-40.
Freeman et al., Copy Number Gains in EGFR and Copy Number Losses in PTEN Are Common Events in Osteosarcoma Tumors, Cancer, 2008, vol. 113:1453-1461.
Jiang et al., Surfactant Protein A Gene Deletion and Prognostics for Patients with Stage I Non-Small Cell Lung Cancer, Clinical Cancer Research, 2005, 11(15), 5417-5424.
Marsit et al, PTEN expression in non-small-cell lung cancer: evaluating its relation to tumor characteristics, allelic loss, and epigenetic alteration, Human Pathology, 2005, vol. 36:768-776.

(Continued)

*Primary Examiner* — Kenneth R. Horlick
*Assistant Examiner* — Joyce Tung
(74) *Attorney, Agent, or Firm* — David A. Casimir; Casimir Jones S.C.

(57) ABSTRACT

The invention provides methods for identifying early stage non-small cell lung cancer (NSCLC) patients who will have a favorable prognosis for the recurrence of lung cancer after surgical resection. The invention is based on the discovery that assessment of chromosomal copy number abnormalities at chromosome 10q23.3 and centromere 10 can be used for prognostic classification. The invention preferably uses fluorescence in situ hybridization with fluorescently labeled nucleic acid probes to hybridize to patient samples to quantify the chromosomal copy number of the these genetic loci. The chromosome copy number can also be determined using, for example, PCR or array CGH. Assessment of the copy number abnormality patterns with a classifier based on the relative loss of 10q23.3 signals compared to the centromere 10 signals produced statistically significant prognostic classification for NSCLC. The ratio of PTEN/CEP 10 signals, using a cutoff of 0.80, was capable of dividing patients into a group of 41 ($\geq$0.80) in which 33 (80.5%) had the favorable prognosis, and a group of 18 (<0.80) in which 6 (33.3%) had the favorable prognosis (p=0.0008). Median times to recurrence in the former and latter groups were 83.0 and 13.0 months, respectively (p<0.0001).

14 Claims, 1 Drawing Sheet

(56) References Cited

OTHER PUBLICATIONS

Mao et al., FBXW7 Targets mTOR for Degradation and Cooperates with PTEN in Tumor Suppression, Science, 2008, vol. 321:1499-1502.

Morrison et al., Effects of ERBB2 Amplicon Size and Genomic Alterations of Chromosomes 1, 3, and 10 on Patient Response to Trastuzumab in Metastatic Breast Cancer, Genes, Chromosomes & Cancer, 2007, vol. 46:397-405.

Sos et al., Predicting drug susceptibility of non-small cell lung cancers based on genetic lesions, J. of Clinical Investigation, 2009, vol. 119 (6), 1727-1740.

Tang et al., Phosphorylated Akt overexpression and loss of PTEN expression in non-small cell lung cancer confers poor prognosis, Lung Cancer, 2006, vol. 51, 181-191.

Varella-Garcia et al, Multi-target interphase fluorescence in situ hybridization assay increases sensitivity of sputum cytology as a predictor of lung cancer, Cancer Detection & Prevention, 2004, vol. 28 (4), 244-251.

Halling et al, A Comparison of Cytology and Fluorescence in Situ Hybridization for the Detection of Lung Cancer in Bronchoscopic Specimens, Chest, 2006, 130:694-701.

Zudaire et al, Molecular characterization of small peripheral lung tumors based on the analysis of fine needle aspirates, Histol. Histophathol., 2008, 23:33-40.

Halling et al., Fluorescense in situ hybridization in diagnostic cytology, Hum. Path. 2007, 38: 1137-1144.

Nath et al, Fluorescence in Situ Hybridization (FISH): DNA Probe Production and Hybridization Critereia, Biotechnic Histochem, 1998, 73 (1), 6-22.

Wheeless et al, Bladder Irrigation Specimens Assayed by Fluorescence in Situ Hybridization to Interphase Nuclei, Cytometry, 1994, 17:319-326.

Morrison et al., Labeling Fluorescence in Situ Hybridization Probes for Genomic Targets, Molecular Cytogenetics: Protocols & Applications, 2002, Chap. 2, 21-40.

Romeo et al., Chromosomal abnormalities in non-small cell lung carcinomas and in bronchial epithelia of high-risk smokers detected by multi-target interphase fluorescence in situ hybridization, Journal of Molecular Diagnostics, May 2003, vol. 5, No. 2, 103-112.

Carlson et al., Chromosome 17 aneusomy detected by fluorescence in situ hybridization in vulvar squamous cell carcinomas and synchronous vulvar skin, American Jorunal of Pathology, Sep. 2000, vol. 157, No. 3, 973-983.

Thisted, R.A., (May 25, 1998) What is a P-value?, from www.stat.uchicago.edu/~thisted, 1-6.

* cited by examiner

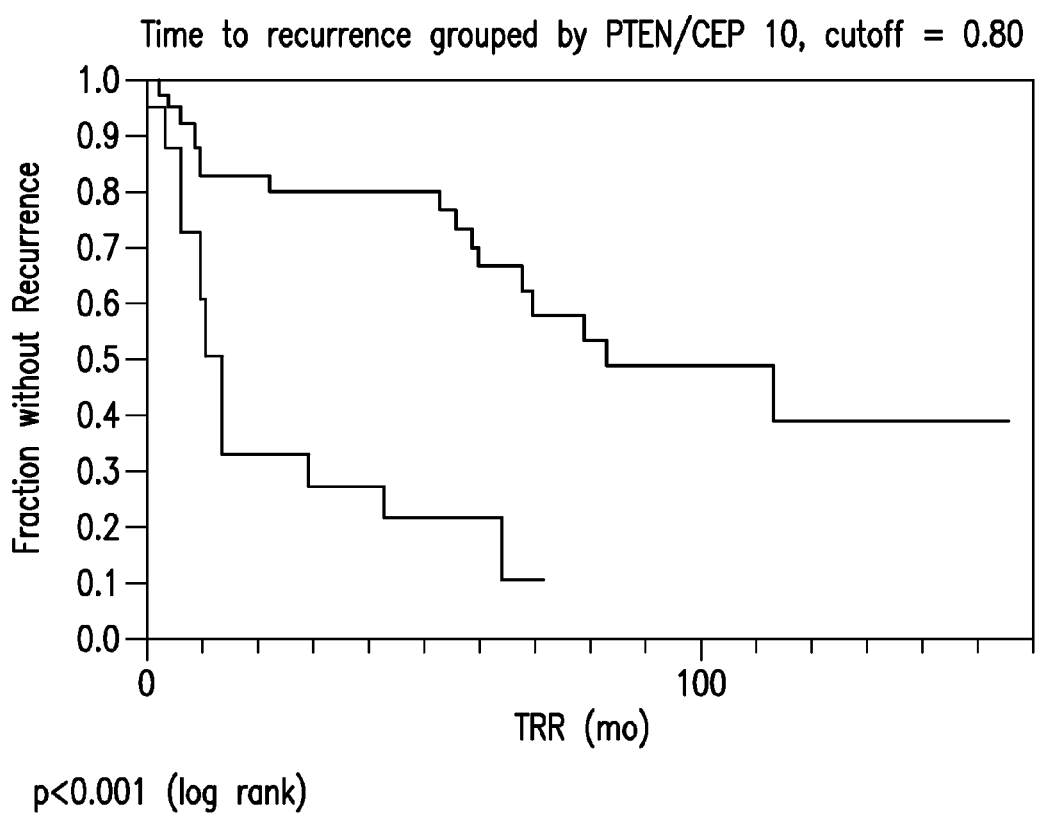

PROGNOSTIC TEST FOR EARLY STAGE NON SMALL CELL LUNG CANCER (NSCLC)

FIELD OF THE INVENTION

The invention relates to an in vitro diagnostic assay of tissue samples from lung cancer patients for determining patient prognosis, and in particular relates to an in vitro assay for determining prognosis of early stage patients, such as those diagnosed with Stage Ib or Stage II non-small cell lung cancer.

BACKGROUND OF THE INVENTION

Lung cancer accounted for almost one third of cancer deaths in the United States in 2005, and is broadly classified into two types: non-small cell lung cancer and small cell lung cancer. Non-small cell lung cancer (NSCLC) comprises 80-85% of lung cancer cases in the United States. The types of NSCLC are named for the kinds of cells found in the cancer and how the cells look under a microscope. NSCLC comprises three major types: (i) Squamous cell carcinoma, which begins in squamous cells, that are thin, flat cells that look like fish scales. Squamous cell carcinoma is also called epidermoid carcinoma; (ii) Large cell carcinoma, which begins in several types of large lung cells; (iii) Adenocarcinoma, which begins in the cells that line the alveoli of the lung and make substances such as mucus. Other less common types of NSCLC include pleomorphic carcinoma, carcinoid tumor and unclassified carcinoma.

Diagnosis of NSCLC is done by a pathologist's examination of suspected tissue, such as a biopsy sample. After NSCLC diagnosis, the patient's disease is assigned a prognosis (the chance of recovery) using the patient's overall health and age, the severity of symptoms such as coughing and difficulty in breathing, the particular type of NSCLC, and the staging of the cancer. Staging takes into account the size of the tumor and whether the tumor is present in the lung only or has spread to other places in the body. The particular treatment options for a NSCLC patient are then selected based upon these considerations, and the cancer staging is an important component for treatment selection. Patients with early stage NSCLC can be potentially cured by surgical resection to remove the tumor, but the current diagnostic modalities are not able to predict which patients will recur after surgery.

The National Comprehensive Cancer Network internet web site describes NSCLC staging as follows. "The system most often used in United States clinical practice to describe the growth and spread of non-small cell lung cancer (NSCLC) is the TNM staging system, also known as the American Joint Committee on Cancer (AJCC) system. In TNM staging, information about the tumor (T), any spread into nearby lymph nodes (N), and any distant organ metastases (M) is combined and a stage is assigned to specific TNM groupings. The grouped stages are described using the number 0 and Roman numerals from I to IV.

"T categories are based on the lung cancer's size, its spread and location within the lungs, and its spread to nearby tissues. In the T is category, the cancer is found only in the layer of cells lining the air passages. It has not spread into other lung tissues. This category is also known as carcinoma in situ.

"In the T1 category, the cancer is no larger than 3 centimeters (slightly less than 1 to 1¼ inches), has not spread to the visceral pleura (membranes that surround the lungs), and does not affect the main branches of the bronchi.

"In the T2 category, the cancer has one or more of the following features: (i) it is larger than 3 cm; (ii) it involves a main bronchus of a lung but is not closer than 2 cm (about 3¼ to 4 inches) to the point where the trachea (windpipe) branches into the left and right main bronchi; or (iii) has spread to the visceral pleura. The cancer may partially block the airways, but this has not caused the entire lung to collapse or develop pneumonia.

"In the T3 category, the cancer has one or more of the following features: (i) it has spread to the chest wall, the diaphragm (the breathing muscle that separates the chest from the abdomen), the mediastinal pleura (the membranes surrounding the space between the 2 lungs), or parietal pericardium (the membranes of the sac surrounding the heart); (ii) it involves a main bronchus of a lung, and it is closer than 2 cm (about 3¼ inch) to the point where the trachea (or windpipe) branches into the left and right main bronchi, but does not involve this area; or (iii) It has grown into the airways enough to cause one lung to entirely collapse or to cause pneumonia of the entire lung.

"In the T4 category, the cancer has one or more of the following features: (i) It has spread to the mediastinum (the space behind the chest bone and in front of the heart), the heart, the trachea (windpipe), the esophagus (the tube connecting the throat to the stomach), the backbone, or the point where the trachea branches into the left and right main bronchi; (ii) Two or more separate tumor nodules are present in the same lobe; or (iii) a malignant pleural effusion is present, which is the existence of fluid containing cancer cells in the space surrounding the lung.

"The N category depends on which, if any, of the lymph nodes near the lungs are affected by the cancer. In the N0 category, the cancer has not spread to any lymph node. In the N1 category, the cancer has spread to lymph nodes within the lung or into the hilar lymph nodes (those located around the area where the bronchus enters the lung). In N1 category the affected lymph nodes are only on the same side as the cancerous lung. In the N2 category, the cancer has spread to subcarinal lymph nodes (those which are around the point where the trachea branches into the left and right bronchi) or to lymph nodes in the mediastinum (the space behind the chest bone and in front of the heart). In the N2 category, the affected lymph nodes are on the same side of the cancerous lung. In the N3 category, the cancer has spread to lymph nodes near the collarbone on either side, and/or to the hilar or mediastinal lymph nodes on the side opposite the cancerous lung.

The M category depends on whether the cancer has metastasized and spread to any distant tissues and organs. In the M0 category, there is no distant cancer spread. In the M1 category, the cancer has spread to 1 or more distant sites. Sites which are considered distant include other lobes of the lungs, lymph nodes further than those used to determine the N category of the cancer, and other organs or tissues such as the liver, bones, or brain.

Once the T, N, and M categories have been assigned for the particular NSCLC, this information is combined (stage grouping) to assign an overall stage of 0, I, II, III, or IV (see Table 1). Various combinations of the T and N categories are combined into stages. The stages identify tumor types that have a similar prognosis and are treated in a similar way. As noted in Table 1, a tumor with distant spread (i.e. an M1 category cancer) is considered Stage IV, regardless of tumor size of involvement of lymph nodes." The following Table from the NCCN internet web site shows the combined category and stage classification for NSCLC.

TABLE 1

| Overall Stage | T Category | N Category | M Category |
|---|---|---|---|
| Stage 0 | Tis | N0 | M0 |
| Stage IA | T1 | N0 | M0 |
| Stage IB | T2 | N0 | M0 |
| Stage IIA | T1 | N1 | M0 |
| Stage IIB | T2 | N1 | M0 |
| | T3 | N0 | M0 |
| Stage IIIA | T1 | N2 | M0 |
| | T2 | N2 | M0 |
| | T3 | N1 | M0 |
| | T3 | N2 | M0 |
| Stage IIIB | Any T | N3 | M0 |
| | T4 | Any N | M0 |
| Stage IV | Any T | Any N | M1 |

NSCLC patients with lower stage numbers generally have a more favorable prognosis and outlook for survival, and these patients are generally treated by surgical resection of the tumor. However, even for early stage patients, such as those with Stage IB, Stage IIA or IIB NSCLC, a significant percentage of these patients will recur after surgical resection with more aggressive disease and die. The current clinical diagnostic methods are incapable of identifying early stage NSCLC prognosis with sufficient accuracy to direct more aggressive therapy against those patients more likely to recur. Better in vitro diagnostic methods to identify higher risk, early stage NSCLC patients who should receive neoadjuvant or adjuvant chemotherapy or even forgo surgical resection altogether, are therefore needed.

Molecular in vitro diagnostic assays based on fluorescence in situ hybridization (FISH) using fluorescently labeled DNA hybridization probes to identify chromosomal abnormalities have been disclosed for use in the selection of chemotherapy for NSCLC patients, see PCT/US2005/018879, "Methods for prediction of clinical outcome to epidermal growth factor inhibitors by cancer patients", M. Garcia et al. FISH assays have also been used as an initial diagnostic assay for NSCLC, see U.S. Patent Application 20060063194, "Methods and probes for the detection of cancer", L. Morrison et al., published Mar. 23, 2006 (hereafter referred to as "Morrison '194"), which is incorporated herein by reference in its entirety. The Morrison '194 application describes multiple FISH probe sets useful for screening and diagnosis of NSCLC, and one probe set described in Morrison '194 is commercially available in Europe as the LAVysion™ probe set from Abbott Molecular, Inc. (Des Plaines, Ill., U.S.A.). The LAVysion probe set was previously commercially available in the U.S. under the U.S. Food and Drug Administration ASR (Analyte Specific Reagent) labeling, for use by clinical laboratories to produce clinical diagnostic assays. The LAVysion ASR probe set comprises four FISH probes: a chromosome 5p15 locus specific probe labeled with the SpectrumGreen green fluorophore, a chromosome 8q24 locus specific probe labeled with the SpectrumGold yellow fluorophore, a chromosome 6 enumeration probe labeled with the SpectrumAqua blue fluorophore, and a chromosome 7p12 locus specific probe labeled with the SpectrumRed red fluorophore.

Multiple research publications describe research performed using the LAVysion probe set, see e.g., M. Garcia et al., "Multi-target interphase fluorescence in situ hybridization assay increases sensitivity of sputum cytology as a predictor of lung cancer", Cancer Detection and Prevention, Vol. 24, Issue 4, 2004: 244-251; K. Halling et al., "A Comparison of Cytology and Fluorescence in Situ Hybridization for the Detection of Lung Cancer in Bronchoscopic Specimens", Chest, 2006; 130:694-701; and I. Zudaire et al., "Molecular characterization of small peripheral lung tumors based on the analysis of fine needle aspirates", Histol. Histophathol. (2008) 23: 33-40. See also the review article K. Halling et al., "Fluoresence in situ hybridization in diagnostic cytology", Hum. Path. (2007) 38: 1137-1144. None of these previous patent applications or publications on FISH assays for NSCLC has disclosed the use of FISH probes to more accurately identify prognosis for early stage NSCLC, in particular, those classified as Stage IB or Stage II. Applicants' co-pending U.S. patent application Ser. No. 12/082,709, "Diagnostic Methods For Determining Prognosis Of Non-Small Cell Lung Cancer", filed Apr. 11, 2008, describes FISH assays to identify early stage NSCLC prognosis using several classification patterns of the FISH probe signals produced with FISH probes specific to the chromosome 5p15 locus, to the chromosome 8q24 locus and to the chromosome 7p12 locus, and one specific for enumeration of chromosome 6. Applicants' co-pending application does not describe FISH assays to determine the relative loss of DNA at the PTEN locus on chromosome 10 DNA for identification of early stage NSCLC prognosis.

SUMMARY OF THE INVENTION

The present invention provides a method of determining prognosis of early stage non-small cell lung cancer in a human by assessment of the copy number of chromosomal 10 DNA, the method comprising: (a) providing a biological sample from the human; (b) contacting the biological sample with a set of chromosomal probes comprising a chromosome 10q23.3 locus specific probe and a chromosome 10 enumeration probe, under conditions sufficient to enable hybridization of probes to chromosomes in the sample, if any; (c) identifying chromosome copy number abnormalities present at each chromosome locus targeted by the probes; and (d) determining prognosis of early stage non-small cell lung cancer in the subject based upon the chromosomal copy number abnormalities identified in step (c). The invention is based on the discovery that detection of abnormal chromosomal copy number of chromosome 10 at the 10q23.3 locus can be used to more accurately identify those early stage NSCLC patients more likely to recur after surgical resection. Using the probe set of the invention, Applicants have identified a distinct classification of early stage NSCLC based on copy number abnormality patterns in the patient sample that separate patients into favorable (never recurred or did not recur within three years post surgery) and unfavorable (recurred before one year or between one and three years post surgery) prognosis. Preferably, the biological sample is a lung tumor tissue biopsy or resection and the sample has been classified as an early stage cancer, for example, such as any of Stage IB, Stage IIA or Stage IIB, using the TNM staging system. The invention preferably uses in situ hybridization and, more preferably, fluorescent in situ hybridization (FISH) with fluorescently labeled nucleic acid probes or fluorescently labeled probes comprising nucleic acid analogs to determine the copy number at each of these loci. Preferred FISH probes for use in the invention comprise a probe specific to the locus of the PTEN gene at 10q23.3 and a probe specific to the centromere of chromosome 10. The chromosome copy numbers used in the invention can also be determined by other methods, including, for example, by array comparative genomic hybridization (array CGH) or polymerase chain reaction (PCR). The invention is particularly beneficial for providing improved prognostic information for early stage NSCLC patients and enables improved therapy selection for those early stage NSCLC patients at higher risk of cancer recurrence.

A FISH assay with a two probe set comprising a probe specific to the chromosome 10q23.3 locus of the PTEN gene and a chromosome enumeration probe specific to the centromere 10 was used to evaluate chromosomal copy number abnormalities in paraffin embedded NSCLC tumor biopsy samples as a prognostic tool for early stage NSCLC in a cohort of 59 patients, in which all had been treated by surgery without chemotherapy. In this cohort, 16 patients developed recurrent lung cancer within one year of surgery; four developed recurrent lung cancer between one and three years after surgery; 14 developed recurrent lung cancer more than three years after surgery; and 25 never developed recurrent cancer, with a minimum of 34.5 months of follow-up after surgery. Various classifiers looking at chromosome 10 copy number patterns were derived from the chromosome copy number abnormalities determined by this two probe FISH assay. A range of cutoff values for each classifier were used to categorize patients into two groups, and times to cancer recurrence in the two groups were compared by contingency tables (2-sided Fischer's exact test p-values) and Kaplan Meyer analysis (log rank p-values). A FISH classifier was found to associate strongly with prognosis when patients that recurred within 3 years of surgery (unfavorable prognosis) were compared to patients that either did not recur or recurred more than 3 years post surgery (favorable prognosis), or when median times to recurrence (TTR) times were compared between patient groups distinguished by the classifiers. That classifier is the presence of PTEN Deletion: cells showing on a cell by cell basis, a ratio of the 10q23.3 probe signal to the chromosome 10 enumeration probe signal of less than 0.80. This classifier provides a statistically significant classification of the patients into favorable and non-favorable prognosis, with a p value of p<0.0001 when optimal thresholds (also referred to as cutoffs) are applied to the parameter as discussed herein. Median times to recurrence in the PTEN Deletion group were 83.1 and 13.0 months, respectively, for the group with ratios greater than or equal to 0.80 and the group with ratios less than 0.80. The methods of the invention are thus able to provide significantly improved prognostic information for early stage NSCLC.

BRIEF DESCRIPTION OF THE DRAWINGS

FIG. 1 is a Kaplan-Meyer curve showing the time to lung cancer recurrence for a 59 patient cohort with early stage NSCLC, classified by the PTEN Deletion ratio.

DETAILED DESCRIPTION OF THE INVENTION

NSCLC Prognosis. The invention includes methods for determining prognosis of NSCLC patients classified as early stage cancers, in particular those classified as Stage IB, Stage IIA or Stage IIB (Stage IIA and IIB are collectively referred to as Stage II) using the widely used TNM staging system. Alternate NSCLC staging systems based upon other diagnostic classifications can be used to identify the patients whose tissue sample may be assayed by the method of the invention. As used herein, an early stage NSCLC refers to a NSCLC tumor that has not spread to more than one lymph node, nor metastasized to any other organ. Early stage NSCLC patients are almost always treated by surgical resection seeking complete tumor removal, yet a significant risk of recurrence exists for these early stage patients even where the tumor is believed completely resected. Current diagnostic modalities do not allow accurate prediction of which of these early stage cancers are high risk for recurrence and thus should be treated post-resection with adjuvant chemotherapy or before the resection using neoadjuvant chemotherapy. The invention provides prognostic identification of those early stage patients at higher risk by determining chromosomal copy number in the patient sample in two copy number assessments: chromosomal locus 10q23.3 and the copy number for chromosome 10. For purposes herein, an early stage NSCLC patient with a favorable prognosis is one that is determined to not have either cancer recurrence or progression of the cancer within three years of surgical resection of the patient's tumor; and an early stage NSCLC patient with an unfavorable prognosis is one that is determined to have either cancer recurrence or progression of the cancer within three years of surgical resection of the patient's tumor.

FISH analysis with two FISH probes, one that hybridized specifically to the locus of the PTEN gene at chromosome 10q23.3 and one that hybridized specifically to the centromere of chromosome 10, was used to evaluate chromosomal copy number abnormalities in paraffin embedded NSCLC tumor biopsy samples as a prognostic tool for early stage NSCLC in a cohort of 59 patients, all of which had been treated by surgery without chemotherapy. In this cohort, 16 patients developed recurrent lung cancer within one year of surgery; four developed recurrent lung cancer between one and three years after surgery; 14 developed recurrent lung cancer more than three years after surgery; and 25 never developed recurrent cancer, with a minimum of 34.5 months of follow-up after surgery. A classifier based on chromosomal copy number abnormality patterns identified using these two probes was found to associate strongly with prognosis when patients that recurred within 3 years of surgery (unfavorable prognosis) were compared to patients that either did not recur or recurred more than 3 years post surgery (favorable prognosis), or when median times to recurrence (TTR) times were compared between patient groups distinguished by the classifiers.

The classifier was used to analyze the hybridization pattern from the two probes in 40 to 120 cells of tissue sample for the presence of a PTEN deletion: the ratio of the number of 10q23.3 probe signals, summed over all enumerated cells, to the number of chromosome 10 enumerator probe signals, summed over all enumerated cells, of less than 0.80. The classifier provides a statistically significant classification of the patients into favorable and non-favorable prognosis, with a p value of p<0.0001. Median times to recurrence in the PTEN deletion groups were 83.1 months for the group of patients with ratios greater than or equal to 0.80 and 13.0 months for the group of patients with ratios less than 0.80. The method of the invention is thus able to provide significantly improved prognostic information for early stage NSCLC.

The prognostic identification of early stage NSCLC of the invention is done on an appropriate biological sample obtained from the patient by in situ hybridization to establish the presence of and pattern of chromosomal abnormalities in the patient sample. In general, in situ hybridization includes the steps of fixing a biological sample, hybridizing one or more chromosomal probes to target DNA contained within the fixed sample, washing to remove non-specifically bound probe, and detecting the hybridized probe. The in situ hybridization can also be carried out with the specimen cells from the biological sample in liquid suspension, followed by detection by flow cytometry.

The identification of NSCLC prognosis of the invention can also be used with other prognostic in vitro diagnostic assays, such as evaluating the expression in the patient sample of suitable proteins such as EGFR, pAKt and PTEN. Patients whose samples are found with expression of such proteins in conjunction with an abnormal chromosomal copy number pattern, that is associated with an unfavorable outcome (poor prognosis), may be eligible for more aggressive post-surgery treatment, such as chemotherapy.

Chromosomal Probes. Suitable probes for use in the in situ hybridization methods utilized with the invention for the detection of abnormal copy number pattern (aneusomy or polysomy) are a combination of a chromosome enumeration probe to chromosome 10 and a chromosome locus specific probe hybridizable to chromosome 10q23.3, preferably at the locus of the PTEN gene, with each probe labeled to be distinguishable from the other. Chromosome enumeration probes hybridize to a chromosomal region, usually a repeat sequence region, and indicate the presence or absence of the target chromosome. As is well known in the art, a chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs, that are referred to as alpha-satellite DNA. A non-limiting example of a specific chromosome enumeration probe is either the SpectrumAqua™ CEPR 10 probe or the SpectrumGreen™ CEPR 10 probe (both from Abbott Molecular, Inc., Des Plaines, Ill.). The SpectrumAqua CEP 10 enumeration probe was used in the Examples below.

The chromosome 10 enumeration probe is used with a locus specific probe for detecting copy number abnormalities at 10q23.3, for example to determine the status of deletion and/or polysomy of these loci. A locus specific probe hybridizes to a specific, non-repetitive locus on a chromosome. It is preferred that the 10q23.3 probe includes at least a portion of the PTEN gene. A preferred locus specific probe is the Vysis LSI PTEN SpectrumOrange probe (10q23), which is available commercially from Abbott Molecular Inc. in a probe set mixed with the Vysis CEP™ 10 SpectrumGreen probe. In the experimental work described below, a PTEN locus specific probe labeled with the SpectrumRed fluorescent label and the commercially available SpectrumAqua CEP 10 probe were used.

Probes that hybridize with centromeric DNA are available commercially from Abbott Molecular Inc. (Des Plaines, Ill.) and Molecular Probes, Inc. (Eugene, Oreg.). Alternatively, probes can be made non-commercially using well known techniques. Sources of DNA for use in constructing DNA probes include genomic DNA, cloned DNA sequences such as bacterial artificial chromosomes (BAC), somatic cell hybrids that contain one or a part of a human chromosome along with the normal chromosome complement of the host, and chromosomes purified by flow cytometry or microdissection. The region of interest can be isolated through cloning or by site-specific amplification via the polymerase chain reaction (PCR). See, for example, Nath, et al., Biotechnic Histochem, 1998, 73 (1): 6-22; Wheeless, et al., Cytometry, 1994, 17:319-327; and U.S. Pat. No. 5,491,224. The starting human DNA used to manufacture useful locus specific probes can be obtained by obtaining a nucleic acid sequence for the locus from the Human Genome database, such as that maintained by the University of California Santa Cruz, and then using that sequence to screen in silico a BAC human DNA library, such as that maintained by the Roswell Park Cancer Center or Invitrogen, to identify useful BAC clones. Synthesized oligomeric DNA probes or probes made from nucleic acid analogs, such as peptide nucleic acid (PNA) probes, can also be used.

The size of the chromosomal region detected by the probes used in the invention can vary, for example, from the alpha satellite 171 base pair probe sequence noted above to a large segment of 900,000 bases. Locus-specific probes that are directly labeled are preferably at least 100,000 bases in complexity, and use unlabeled blocking nucleic acid, as disclosed in U.S. Pat. No. 5,756,696, herein incorporated by reference, to avoid non-specific binding of the probe. It is also possible to use unlabeled, synthesized oligomeric nucleic acid or unlabeled nucleic acid analogs, such as a peptide nucleic acid, as the blocking nucleic acid.

The chromosomal probes can contain any detection moiety that facilitates the detection of the probe when hybridized to a chromosome. Effective detection moieties include both direct and indirect labels as described herein. Examples of detectable labels include fluorophores (i.e., organic molecules that fluoresce after absorbing light), radioactive isotopes (e.g., $^{32}$P, and $^{3}$H) and chromophores (e.g., enzymatic markers that produce a visually detectable marker). Fluorophores are preferred and can be directly labeled following covalent attachment to a nucleotide by incorporating the labeled nucleotide into the probe with standard techniques such as nick translation, random priming, and PCR labeling. Alternatively, deoxycytidine nucleotides within the probe can be transaminated with a linker. The fluorophore can then be covalently attached to the transaminated deoxycytidine nucleotides. See, e.g., U.S. Pat. No. 5,491,224 to Bittner, et al., which is incorporated herein by reference. Useful probe labeling techniques are described in Molecular Cytogenetics: Protocols and Applications, Y.-S. Fan, Ed., Chap. 2, "Labeling Fluorescence In Situ Hybridization Probes for Genomic Targets", L. Morrison et. al., p. 21-40, Humana Press, © 2002, incorporated herein by reference.

Examples of fluorophores that can be used in the methods described herein are: 7-amino-4-methylcoumarin-3-acetic acid (AMCA), Texas Red™ (Molecular Probes, Inc., Eugene, Oreg.); 5-(and -6)-carboxy-X-rhodamine, lissamine rhodamine B, 5-(and -6)-carboxyfluorescein; fluorescein-5-isothiocyanate (FITC); 7-diethylaminocoumarin-3-carboxylic acid, tetramethylrhodamine-5-(and -6)-isothiocyanate; 5-(and -6)-carboxytetramethylrhodamine; 7-hydroxycoumarin-3-carboxylic acid; 6-[fluorescein 5-(and -6)-carboxamido]hexanoic acid; N-(4,4-difluoro-5,7-dimethyl-4-bora-3a,4a diaza-3-indacenepropionic acid; eosin-5-isothiocyanate; erythrosine-5-isothiocyanate; 5-(and -6)-carboxyrhodamine 6G; and Cascade™ blue acetylazide (Molecular Probes, Inc., Eugene, Oreg.). In the preferred probe set, fluorophores of different colors are used such that each chromosomal probe in the set can be distinctly visualized.

After hybridization, the probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detection molecules or further processing are then required to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. Such enzymatic markers can be detected in standard calorimetric reactions using a substrate for the enzyme. Substrates for alkaline phosphatase include 5-bromo-4-chloro-3-indolylphosphate and nitro blue tetrazolium. Diaminobenzidine can be used as a substrate for horseradish peroxidase.

The probes and probe sets useful with the methods of the invention can be packaged with other reagents into kits to be used in carrying out the methods of the invention.

Preferred Probe Set. A preferred probe composition comprises a mixture of two directly labeled DNA FISH probes: the SpectrumOrange LSI PTEN probe that covers an approximately 370 kb region 10q23, including sequences that flank the 3' and 5' end of the PTEN gene; and the CEP 10 SpectrumGreen probe that hybridizes to the alpha satellite DNA region located at the centromere of chromosome 10 (10p11.1-q11). The LSI PTEN SpectrumOrange/CEP 10 SpectrumGreen probe set is available commercially from Abbott Molecular Inc. premixed in a suitable hybridization buffer.

Preparation of Samples. A biological sample is a sample that contains cells or cellular material, including cell-containing extracts from a patient sample. For example, lung samples are typically cells or cellular material derived from pulmonary structures, including but not limited to lung parenchyma, bronchioles, bronchial, bronchi, and trachea. Non-limiting examples of biological samples useful for the detection of lung cancer include bronchial specimens, resected lung tissue, lung biopsies, and sputum samples. Examples of bronchial specimens include bronchial secretions, washings, lavage, aspirations, and brushings. Lung biopsies can be obtained by methods including surgery, bronchoscopy, fine needle aspiration (FNA), and transthoracic needle biopsy. In one example, touch preparations can be made from lung biopsies. The inventive assays can also be performed on a circulating tumor cell sample derived from a blood sample from an early stage NSCLC patient. A circulating tumor cell sample can be prepared using the immunomagnetic separation technology available from Immunicon.

Tissues can be fixed with a fixative such as formaldehyde and then embedded in paraffin. Sections are then cut using a microtome and are applied to a microscope slide. Cytology specimens can be prepared from cellular suspensions derived from FNA, bronchial washings, bronchial lavage, or sputum, or disseminated tissue cells. Cytology specimens can be prepared by fixation of cells in ethanol or methanol:acetic acid combined with cytocentrifugation, thin layer deposition methods (e.g. ThinPrep, Cytyc Corp.), smears, or pipetting onto microscope slides. In addition, biological samples can include effusions, e.g., pleural effusions, pericardial effusions, or peritoneal effusions.

In Situ Hybridization Methods. Any suitable in situ hybridization method can be used. Prior to in situ hybridization, chromosomal probes and chromosomal DNA contained within the cell each are denatured. If the chromosomal probes are prepared as a single-stranded nucleic acid, then denaturation of the probe is not required. Denaturation typically is performed by incubating in the presence of high pH, heat (e.g., temperatures from about 70.degree. C. to about 95.degree. C.), organic solvents such as formamide and tetraalkylammonium halides, or combinations thereof. For example, chromosomal DNA can be denatured by a combination of temperatures above 70.degree. C. (e.g., about 73.degree. C.) and a denaturation buffer containing 70% formamide and 2.×SSC (0.3M sodium chloride and 0.03 M sodium citrate). Denaturation conditions typically are established such that cell morphology is preserved. For example, chromosomal probes can be denatured by heat, e.g., by heating the probes to about 73.degree. C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base compositions, complexities, and lengths of the probes, as well as salt concentrations, temperatures, and length of incubation. For example, in situ hybridizations are typically performed in hybridization buffer containing 1-2.×.SSC, 50-55% formamide, a hybridization acceleratant (e.g. 10% dextran sulfate), and unlabeled blocking DNA to suppress non-specific hybridization. In general, hybridization conditions, as described above, include temperatures of about 25 degree C. to about 55 degree C., and incubation lengths of about 0.5 hours to about 96 hours. More particularly, hybridization can be performed at about 32 degree C. to about 45 degree C. for about 2 to about 16 hours.

Non-specific binding of chromosomal probes to DNA outside of the target region can be removed by a series of washes with a salt solution. Temperature and concentration of salt in each wash depend on the desired stringency. For example, for high stringency conditions, washes can be carried out at about 65.degree. C. to about 80.degree. C., using 0.2.× to about 2.×.SSC, and about 0.1% to about 1% of a non-ionic detergent such as Nonidet P-40 (NP40). Stringency can be lowered by decreasing the temperature of the washes or by increasing the concentration of salt in the washes.

The hybridization of the probes to the tissue sample can be performed manually, or with the assistance of instruments, such as the ThermoBrite hybridization oven, the VP 2000 Processor, or the XMatrix™ processing instrument (all available commercially from Abbott Molecular, Inc.).

Pre-Selection of Cells. Cell samples can be evaluated preliminarily by a variety of methods and using a variety of criteria. The probes and methods described herein are not limited to usage with a particular screening methodology. One example is the "scanning method" wherein the observer scans hundreds to thousands of cells for cytologic abnormalities, e.g., as viewed with a DAPI filter. The number of cells assessed will depend on the cellularity of the specimen, which varies from patient to patient. Cytologic abnormalities commonly but not invariably associated with dysplastic and neoplastic cells include nuclear enlargement, nuclear irregularity, and abnormal DAPI staining (frequently mottled and lighter in color). In the scanning step, the observer preferably focuses the evaluation of the cells for chromosomal abnormalities (as demonstrated by FISH) to those cells that also exhibit cytological abnormalities. In addition, a proportion of the cells that do not have obvious cytologic abnormalities can be evaluated since chromosomal abnormalities also occur in the absence of cytologic abnormalities. This scanning method is described in further detail in U.S. Pat. No. 6,174,681 to Halling, et al., which is incorporated herein by reference. Lung cancer cells can be selected for evaluation using the method described in US Patent Pub. 2003/0087248 A1 by Morrison, et al., which is incorporated herein by reference.

Regions of the specimen may also be selected for evaluation using conventional stains, such as stains containing hematoxylin and eosin. For example, a pathologist can stain a section of a paraffin-embedded specimen with a hematoxylin/ eosin stain, identify a region as probably cancerous by tissue morphology and staining pattern, and outline that region with a felt tip ink pen or glass scribe. The marked region is then transferred to the corresponding location on a serial section of the paraffin-embedded specimen with a glass scribe, and FISH is performed on that slide. Cells within the scribed region are then evaluated for FISH signals, Detection of Classification Patterns of Chromosomal Abnormality. Abnormal cells are characterized by the presence of one or more patterns of chromosomal copy number abnormalities. The presence of a copy number abnormality pattern in a cell in the patient sample is assessed by examining the hybridization pattern of the chromosomal probe (e.g., the number of signals for each probe) in the cell, and recording the number of signals. Aneusomy is typically intended to mean abnormal copy number, either of the whole chromosome or a locus on a chromosome. Abnormal copy number includes both monosomy (one copy) and nullsomy (zero copies) of the autosomes, also referred to as a deletion, and greater than 2 copies, which for a particular chromosomal locus is sometimes referred to as gene amplification (alternatively, amplification is reserved for the situation in which the gene copy number exceeds the copy number of the chromosome in which it is contained). However, sectioning of paraffin-embedded specimens (typically 4-6 µm) may result in truncation of cell nuclei such that the number of FISH signals per cell for some cells will be somewhat lower than the actual number of copies in an intact nucleus. In the classifier of the invention, the absolute number of particular FISH probe hybridization signals for each probe is determined and then used in ratio comparisons.

Test samples can comprise any number of cells that is sufficient for a clinical diagnosis, and in a preferred paraffin-embedded tissue sample, the hybridization pattern is typically assessed in about 20 to about 200 cells. It is preferred to assess the hybridization pattern in about 40 to about 120 cells per sample.

The PTEN deletion ratio classifier determined the ratio of PTEN locus probe hybridization signals, summed over all 40 to 120 cells enumerated, to the probe signals for the chromosome 10 enumeration probe summed over all cell 40 to 120 cells enumerated The PTEN ratio using a cutoff of a ratio of less than 0.80 was capable of dividing patients into a group of 41 patients (ratio ≥0.8) in which 33 of these patients (80.5%) had the favorable prognosis, and a group of 18 patients (ratio <0.80) in which only 6 (33.3%) had the favorable prognosis (p=0.0008). Median times to recurrence in the former and latter groups were 83.1 and 13.0 months, respectively (p<0.0001). FIG. 1 is a Kaplan-Meyer plot of the time to lung cancer recurrence for the favorable and unfavorable patient prognostic groups identified by the PTEN/Chromosome 10 ratio classifier.

It is also within the scope of invention to determine in the patient tissue sample, the chromosomal copy number at the PTEN locus and the overall chromosome 10 copy number for use with the classifier of the invention, by using other methods than in situ hybridization, such as by PCR or by array CGH using any suitable nucleic acid microarray hybridization target including oligonucleotide arrays. Any suitable PCR or microarray method for measuring the chromosomal copy numbers is useful in the invention. J.-H. Mao et al., "FBXW7 Targets mTOR for Degradation and Cooperates with PTEN in Tumor Suppression", Science, Vol. 321, 12 Sep. 2008, 1499-1502, describes determination of chromosome copy number at the locus of PTEN in breast cancer cell lines using PCR (the PCR methodology used by Mao et al. is described in the Supplementary Materials to the Science article, available at the Science Internet web site: sciencemag.org. The Mao et al. PCR copy number assay was a Taqman assay, using PCR primers designed using the Primer Express Oligo Design Software v. 1.0 (Applied Biosystems, Foster City, Calif.) specifically for a Taqman assay. The PCR amplification was performed on the DNA extracted from various breast cancer cell lines in an ABI 7700 instrument (Applied Biosystems) in a 50 microliter reaction mix of 1× Taqman Universal PCR Master Mix (Applied Biosystems), 1.6 nM primer, 0.4 nM Taqman detector probe and 12.5 ng DNA. Mao et al. used PCR cycling conditions of 95 degrees Centigrade for 12 min. for 1 cycle, then forty cycles of 95 degrees Centigrade for 20 sec. 60 degrees Centigrade for 20 sec., then 72 degrees Centigrade for 60 seconds. The chromosome copy number was determined from the PCR cycle number (CT) at which the DNA fluorescence reached a threshold amount of fluorescence above background. Normalization of differences in the amount of input DNA was done by amplification at a reference DNA once per plate done in triplicate. The CT values for each set of triplicates was averaged. The copy number at the PTEN locus in each cell line was determined by subtracting the CT at the reference locus from the PTEN CT value. The chromosome copy number gain or loss for the breast cancer cell lines was determined by subtracting from the CT determined for each line the value of a normal CT for PTEN calculated from the average of the CT determined for each of six normal genomic DNA samples. The difference between the cell line CT and the normal CT was interpreted as a copy number gain if the difference was greater than 0.5, and as a copy number loss if the difference was less than or equal to 0.5. The PCR method of Mao et al. does not disclose measurement of chromosome copy number of the PTEN locus and of chromosome 10 for determining recurrence of early stage NSCLC. The Mao et al. method can be applied to determine chromosome copy number for use in the method of the invention, by starting with a genomic DNA extract from the NSCLC tissue sample, instead of the breast cancer cell line extracts of Mao et al. In using PCR or any microarray analysis of copy number, care must be taken to perform the necessary DNA extraction from primarily NSCLC tumor cells of the sample to avoid contamination with normal cells.

Measurement of chromosomal copy number by array CGH is disclosed in S. Freeman et al., "Copy Number Gains in EGFR and Copy Number Losses in PTEN Are Common Events in Osteosarcoma Tumors", Cancer, Sep. 15, 2008, Vol. 113, No. 6: 1454-1461. Freeman et al. determined the chromosomal copy number at the PTEN locus in frozen osteosarcoma samples by array CGH using an oligonucleotide microarray target. Freeman et al. used 250 ng of genomic DNA from each osteosarcoma sample, which were then digested to completion using the Xba-I restriction endonuclease and ligated to an adaptor containg a generic primer sequence. Three aliquots of each ligated DNA were then amplified under conditions suitable to enrich for 250 to 2500 base pair fragments, and then pooled and purified. The pooled DNA was then fragmented with deoxyribonuclease I and end-labeled with a biotinylated nucleotide using terminal deoxynucleotidyl transferase. The labeled DNA was then mixed with probe array controls and blocking DNA comprising herring sperm DNA and human Cot-1 DNA to produce a hybridization cocktail, which was hybridized to Affymetrix Mapping 50K Xba-1 240 microarray (Affymetrix, Santa Clara, Calif.). After hybridization, the microarrays were stringently washed and stained with streptavidin phycoerythrin (Invitrogen, Carlsbad, Calif.) using the Affymetrix Fluidics Station 400. The hybridized microarrays were scanned with an Affymetrix GeneChip Scanner 3000 and the scanning data analyzed using the Affymetrix Gene DNA Analysis Software v.3.0. The chromosomal copy numbers were determined from the scanning data using the dChipSNP software. First, the scanning data was normalized to a baseline microarray having median signal intensity at the probe intensity level with the invariant set normalization method. After this normalization, the signal values for each SNP target in the microarray were obtained with a model-based (perfect match/mismatch difference model) method. The signal intensities at each SNP target in each of the tumor samples were compared with those from a reference set of 61 normal samples, and the chromosome copy numbers inferred using a hidden Markov model. Freeman et al. do not disclose nor suggest determination of NSCLC recurrence using chromosomal copy number of PTEN. The method of Freeman et al. starting with a NSCLC tissue sample is useful for the determination of chromosomal copy number to be used in the method of the invention.

Details of the invention are further described in the following examples, which are not intended to limit the scope of the invention as claimed. One of skill in the art will recognize that variations and modifications of the invention may be apparent upon reviewing the instant specification. It is therefore an object to provide for such modifications and variations of the embodiments described herein, without departing from the scope or the spirit of the invention.

EXAMPLES

Experimental Methods

Specimens. Tissue specimens from 59 NSCLC patients were obtained from the archives of the Pathology Department of Rush University Medical Center (Chicago, Ill.). All patients had been diagnosed as Stage Ib or Stage II, and were treated with surgical resection without any follow-up or neoadjuvant chemotherapy. Chart review and study analyses were approved by the RUMC Institutional Review Board. The diagnosis of early stage NSCLC in the archival material was obtained from pathology reports. Times to recurrence of lung cancer were obtained from the patient charts. Of the 59 patients, 16 had recurrent lung cancer within one year, four had recurrent lung cancer between one and three years, 14 had recurrent lung cancer after 3 years and 25 never recurred (with 34.5 months minimum follow-up).

In Situ Hybridization. Copy number analyses were performed using a four probe FISH panel, described in and referred to as "Panel 2" in L. Morrison et al., "Effects of ERBB2 Amplicon Size and Genomic Alterations of Chromosomes 1, 3 and 10 on Patient Response to Trastuzumab in Metastatic Breast Cancer", Genes, Chromosomes & Cancer 46:397-405 (2007), herein incorporated by reference and hereafter referred to as "Morrison Amplicon Size", comprising the commercially available CEP 3 SpectrumGreen probe (Abbott Molecular Inc.) hybridizing to the pericentromeric locus of chromosome 3, an experimental probe PIK3CA SpectrumGold hybridizing to the locus of PIK3CA, an experimental PTEN Spectrum Red probe, and the commercially available CEP 10 SpectrumAqua probe (Abbott Molecular Inc.) that was hybridized to the patient specimen. The PTEN SpectrumRed probe was made using the FISH probe manufacturing method described in U.S. Pat. No. 5,506,350, M. Bittner et al., "Production of chromosome region specific DNA sequences and transamination", issued Apr. 9, 1996. The starting human DNA used in the Bittner et al. method was contained in two BAC clones, RP11 380q5 and RP11 11o21, both obtained from Invitrogen (Carlsbad, Calif.). The human DNA insert in these two clones overlaps and the combined human DNA from these clones spans the PTEN locus at 10q23.3, containing sequences that hybridize to both sides of the PTEN locus. The cloned DNA was labeled by condensation with the sulfonyl chloride moiety of the SpectrumRed fluorophore obtained from Molecular Probes (Eugene, Oreg.). After purification, the PTEN probe was mixed with the other probes in a hybridization cocktail described in Morrison Amplicon Size. Specimen slides were prepared using either the Vysis Paraffin Pretreatment II or III kits (Abbott Molecular Inc.). The prepared specimen slides were hybridized with the four FISH probe solution in a HYBrite™ automated co-denaturation oven (Abbott Molecular Inc.). The slides were placed on the oven surface and 10 □L probe solution was layered over the tissue section. A cover slip was applied over the probe solution and sealed to the slide with rubber cement. After denaturation at 73° C. for 5 minutes, the probe was hybridized at 37° C. for 16-18 hr. Following hybridization and removal of the rubber cement seal, the slides were placed in room-temperature 2×SSC (SSC=0.3 M NaCl, 15 mM sodium citrate), 0.3% Nonidet P40 (NP40) for 2-5 min to detach the cover slips. The slides were then immersed in 73° C. 2×SSC, 0.3% NP40 for 2 min to remove nonspecifically bound probe and then were allowed to dry in the dark. DAPI I antifade solution (Abbott Molecular Inc.) was applied to the specimen for visualization of the nuclei. Some of the specimens required additional processing to yield optimal FISH results.

The FISH slides were evaluated under a Zeiss Axioscope epi-fluorescence microscope (Carl Zeiss, Thornwood, N.Y.). Signals were visualized and counting performed with a DAPI single-band-pass filter set to visualize nuclei, a Red single-band-pass filter set to visualize the SpectrumRed-labeled 10q23.3 probe and an Aqua single-band-pass filter set to visualize the SpectrumAqua-labeled CEP 10 probe (all filter sets from Abbott Molecular Inc.). Only nuclei with morphology characteristic of malignant cells were counted. When a slide was counted multiple times, counts were combined and used for recalculating the hybridization signal ratios and signal patterns. FISH signals were enumerated in 40 to 120 cells (mean=65 cells) per specimen to obtain copy numbers for each of the four loci.

A range of cutoff points were analyzed by first generating cutoffs from the mean minus 2 standard deviations to the mean plus 2 standard deviations, in 0.1 standard deviation increments, for each parameter (ratios and % gains), using the mean and standard deviations of the patients with the favorable prognosis (patients that did not recur or recurred after 3 years). Each ratio and % signal gains or loss at each cutoff were compared with time to disease recurrence (greater than or less than 3 years to recurrence) in contingency tables. Cutoffs with the lowest chi-square probabilities were selected for further analysis. No copy number abnormality pattern in the FISH signal data for the PIK3CA and CEP 3 probes relating to disease recurrence was identified.

Statistical Methods. Association between selected classifiers and outcomes was performed using the Fisher's Exact Test. The level of significance was p<0.05 in two-tailed estimates. The Kaplan-Meier method was used to determine median time to recurrence, with comparison between groups assessed by log-rank test (p<0.05 significance).

Results

Several classifications were found to associate strongly with prognosis when patients that recurred within 3 years of surgery (the unfavorable prognosis group) were compared to patients that either did not recur or recurred more than 3 years post surgery (the favorable prognosis group), or when median times to recurrence (TTR) times were compared between patient groups distinguished by the classifiers.

PTEN Deletion Ratio classifier. This classifier determined the ratio of the total number of PTEN signals, summed over all cells enumerated for a specimen, divided by the total number of CEP 10 signals, summed over all cells enumerated for that specimen. The PTEN deletion classifier, using a cutoff of 0.8 for the ratio of PTEN/CEP10, was capable of dividing patients into a group of 41 (≥0.8 PTEN/CEP10) in which 33 (80.5%) had the favorable prognosis, and a group of 18 (<0.8 PTEN/CEP10) in which only 6 (33.3%) had the favorable prognosis (p=0.0008). Median times to recurrence in the former and latter groups were 83.1 and 13.0 months, respectively (p<0.0001). Table 1 shows the data for this classifier. FIG. 1 shows a Kaplan-Meyer plot of time to recurrence (TTR) in the two groups, with the upper curve representing the group of 41 patients (Deletion Ratio (≥0.8 PTEN/CEP10) and the lower curve representing the group of 18 patients (Deletion Ratio <0.8 PTEN/CEP10).

TABLE 1

Outcome grouped by PTEN/Chromosome 10 ratio, cutoff = 0.80

| FISH status | No recurrence or recurrence after 3 yr | Recurrence less than 3 yr | Total patients |
|---|---|---|---|
| ≥0.80 | 33 pts<br>80.5% | 8 pts<br>19.5% | 41 pts |
| <0.80 | 6 pts<br>33.3% | 12 pts<br>66.7% | 18 pts |
| Total patients | 39 pts | 20 pts | 59 pts | p = 0.0008

Discussion of Results

These data indicate that use of genomic copy number assessment of the PTEN and chromosome 10 centromere loci measured by FISH, and with use of an appropriate classifier, is of prognostic importance in early stage NSCLC. The classifier was able to produce statistically significant classification of patients who had been treated with surgery without neoadjuvant or follow-up chemotherapy into favorable and unfavorable recurrence categories. No present clinical in vitro diagnostic assay provides this capability. This data and those in Applicant's co-pending US application, are the first to classify early stage NSCLC patients with no distant metastasis or with spread to no more than one lymph node into favorable and unfavorable prognostic groups on a statistically significant basis using a molecular hybridization assay. FISH assays to the chromosomal loci PTEN and centromere 10 performed on early stage NSCLC biopsy specimens or resected tumors appear valuable in decisions related to surgery and adjuvant therapy.

The associations in the classifier were also fairly robust, in that statistical significance could be found over a range of cutoffs values as wide as about 0.6 to about 1.0 for the PTEN/CEP10 parameter. The cutoff presented in the data for the PTEN/CEP10 classifier is the one that had the lowest p-value (p<0.0001). This means that the cutoff of the ratio used in the PTEN deletion classifier may be varied from that of the cutoff used in the specific analysis shown here.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below.

What is claimed is:

1. A method of determining prognosis of lung cancer in a human patient, the method comprising:
    (a) obtaining a biological sample from a human patient classified as having early stage non-small cell lung cancer;
    (b) contacting the biological sample with a set of chromosomal probes comprising at least two probes selected from the group consisting of a chromosome 10q23.3 locus specific probe and a chromosome 10 enumeration probe under conditions sufficient to enable hybridization of probes in the set to chromosomes in the sample, if any;
    (c) identifying a hybridization pattern of the set of chromosomal probes to the biological sample; and
    (d) determining prognosis of lung cancer in the subject based upon the hybridization pattern identified in step (c), wherein the hybridization pattern is identification of a ratio of the number of probe signals for the chromosome locus 10q23.3 to the number of probe signals of chromosome 10, wherein a ratio of less than 0.80 indicates non favorable prognosis.

2. The method of claim 1, wherein the biological sample comprises a lung tissue biopsy or resection.

3. The method of claim 1, wherein each of the chromosomal probes is directly labeled with a fluorescent label that can be separately detected.

4. The method of claim 1, wherein the biological sample is from a patient classified as having Stage 1b non-small cell lung cancer.

5. The method of claim 1, wherein the biological sample is from a patient classified as having Stage 2 non-small cell lung cancer.

6. The method of claim 1, wherein the contacting step (b) is performed on an automated instrument.

7. The method of claim 1 wherein the cutoff for the ratio, which divides the patient population into two groups of differing prognosis, is from about 0.6 to about 1.0.

8. The method of claim 1 where the cutoff for the ratio, which divides the patient population into two groups of differing prognosis, is about 0.8.

9. The method of claim 1, wherein the biological sample comprises a cytology sample.

10. The method of claim 1, wherein the chromosome 10q23.3 locus specific probe includes sequences that flank each end of phosphatase and tensin homolog (PTEN).

11. A method of determining prognosis of lung cancer in a human patient, the method comprising:
    (a) obtaining a biological sample from a human patient classified as having early stage non-small cell lung cancer;
    (b) measuring in the biological sample both chromosome copy number at chromosome locus 10q23.3 and chromosome copy number for chromosome 10; and
    (c) determining prognosis of lung cancer in the subject based upon ratio of chromosome copy number at chromosome locus 10q23.3 to chromosome copy number for chromosome 10, wherein the cutoff for the ratio, which divides a patient population into two groups of differing prognosis, is from about 0.6 to about 1.0.

12. The method of claim 11, wherein the chromosome copy number at chromosome locus 10q23.3 and for chromosome 10 is measured by in situ hybridization.

13. The method of claim 11, wherein the chromosome copy number at chromosome locus 10q23.3 and for chromosome 10 is measured by polymerase chain reaction.

14. The method of claim 11, wherein the chromosome copy number at chromosome locus 10q23.3 and for chromosome 10 is measured by array comparative genomic hybridization.

* * * * *